US010981118B2

(12) United States Patent
    Collins

(10) Patent No.: US 10,981,118 B2
(45) Date of Patent: Apr. 20, 2021

(54) METHOD AND APPARATUS FOR PURIFYING THE DISPERSING LIQUID IN A COLLOIDAL DISPERSION

(71) Applicant: Conor Collins, Monroe, NY (US)

(72) Inventor: Conor Collins, Monroe, NY (US)

( * ) Notice: Subject to any disclaimer, the term of this patent is extended or adjusted under 35 U.S.C. 154(b) by 246 days.

(21) Appl. No.: 15/653,799

(22) Filed: Jul. 19, 2017

(65) Prior Publication Data
    US 2018/0021729 A1    Jan. 25, 2018

Related U.S. Application Data

(60) Provisional application No. 62/364,819, filed on Jul. 20, 2016.

(51) Int. Cl.
    *B01D 63/04*    (2006.01)
    *A61K 31/05*    (2006.01)
    (Continued)

(52) U.S. Cl.
    CPC ............ *B01D 63/04* (2013.01); *A61K 9/10* (2013.01); *A61K 31/05* (2013.01); *B01D 15/08* (2013.01);
    (Continued)

(58) Field of Classification Search
    CPC .... B01D 15/00; B01D 17/02; B01D 17/0202; B01D 29/00; B01D 29/01; B01D 29/50; B01D 29/52; B01D 29/60; B01D 35/00; B01D 35/30; B01D 35/301; B01D 36/02; B01D 37/00; B01D 37/04; B01D 61/58; B01D 2221/10; B01D 2257/70;
    (Continued)

(56) References Cited

U.S. PATENT DOCUMENTS 4,212,744 A * 7/1980 Oota ..................... A61M 1/16
                                                210/321.64
5,147,550 A * 9/1992 Wijmans .............. B01D 53/225
                                                210/321.6
(Continued)

OTHER PUBLICATIONS

Lenntech, Venturi, Feb. 7, 2008, Captured online Oct. 15, 2019 (Year: 2008).*

(Continued)

*Primary Examiner* — Joseph W Drodge

(57) ABSTRACT

A purification system for a colloidal dispersion containing an unwanted dissolved substance in the dispersing liquid phase is described which includes a back-pressure regulating feature, disposed in a first conduit and downstream of a semi-permeable filter element. This is used to force a portion of the unpurified dispersing liquid across the filter element and into a second conduit. The second conduit is associated with an adsorptive element that serves to remove the unwanted dissolved substance from the filtered portion of the dispersing liquid. A mixing chamber is disposed downstream of the back-pressure regulating feature whereby the purified dispersing liquid portion from the second conduit rejoins the bulk flow of the colloidal dispersion passing through the first conduit. In a preferred embodiment, hollow fibers are used which serve as the back-pressure regulating feature, the adsorptive element, and the mixing chamber before being discharged at the outlet of the device.

6 Claims, 6 Drawing Sheets

(51) Int. Cl.
*A61K 9/10* (2006.01)
*B01D 15/08* (2006.01)
*C02F 1/28* (2006.01)
*C02F 1/44* (2006.01)
*B01D 63/02* (2006.01)

(52) U.S. Cl.
CPC .............. *B01D 63/043* (2013.01); *C02F 1/28* (2013.01); *C02F 1/44* (2013.01); *B01D 63/024* (2013.01); *B01D 2311/06* (2013.01); *B01D 2311/2626* (2013.01); *B01D 2313/08* (2013.01); *B01D 2319/022* (2013.01); *B01D 2319/025* (2013.01); *C02F 2209/03* (2013.01)

(58) Field of Classification Search
CPC ............ B01D 2257/93; B01D 2311/08; B01D 2311/14; B01D 2311/26; B01D 2311/2626; B01D 2311/2649; B01D 2313/00; B01D 2313/08; B01D 2313/083; B01D 2313/086; B01D 2313/24; B01D 2313/40; B01D 2315/10; B01D 35/99; B01D 2201/30; B01D 2313/19; B01D 63/02; B01D 63/024; B01D 63/04; B01D 63/043; B01D 69/08; B01D 2311/2313; B01D 2311/04; B01D 2311/10; B01D 2311/105; B01D 2311/12; B01D 2311/125; B01D 2311/19; B01D 2311/40; B01D 2319/02; B01D 2319/022; B01D 2319/025; B01D 2319/027; B01D 2319/06; B01D 15/08; B01D 2311/06; A61K 31/05; A61K 9/10; C02F 1/28; C02F 1/44; C02F 2209/03
USPC ....... 210/660, 661, 679, 680, 690, 691, 692, 210/693, 694, 767, 790, 799, 806, 807, 210/808, 254, 256, 258, 259, 262, 263, 210/264, 266, 284, 290, 294, 295, 314, 210/316, 321.6, 321.65, 321.72, 321.75, 210/322, 323.2, 340, 348, 428, 417, 210/433.1, 434, 446, 500.23, 321.61, 210/321.79, 321.8
See application file for complete search history.

(56) References Cited

U.S. PATENT DOCUMENTS

| | | | | |
|---|---|---|---|---|
| 5,405,528 | A * | 4/1995 | Selbie ................. | B01D 35/303 210/232 |
| 6,270,674 | B1 * | 8/2001 | Baurmeister .......... | B01D 15/08 210/321.79 |
| 6,635,179 | B1 * | 10/2003 | Summerton .......... | A61L 2/0017 210/321.8 |
| 8,945,387 | B2 * | 2/2015 | Adams .................... | C02F 1/44 210/321.88 |
| 2003/0111414 | A1 * | 6/2003 | Baurmeister ...... | B01J 20/28052 210/641 |
| 2005/0126966 | A1 * | 6/2005 | Tanida .................... | C02F 1/444 210/137 |
| 2007/0163943 | A1 * | 7/2007 | Collins ................ | B01D 63/021 210/335 |
| 2011/0155657 | A1 * | 6/2011 | Collins ............... | A61M 1/1656 210/232 |
| 2015/0343386 | A1 * | 12/2015 | Labib ................... | C11D 3/3956 210/636 |

OTHER PUBLICATIONS

Babl, J., A. Doenicke, and V. Mönch. "New Propofol LCT/MCT Fat Emulsions as Solvent, Approach to Reducing Pain on Injection of Propofol," Eur Hosp Pharmacy (1995): n. pag. Web.

Cai, Weihui, Wanding Deng, and Huihui Yang. "A Propofol Microemulsion with Low Free Propofol in the Aqueous Phase: Formulation, Physicochemical Characterization, Stability and Pharmacokinetics:" International Journal of Pharmaceutics 436.1-2 (2012): 538-44, Web.

Davies, A. F., B. Vadodaria, B. Hopwood, T. Dexter, and D. Conn. "Efficacy of Microfiltration in Decreasing Propofol-induced Pain". Anaesthesia 57.8 (2002): 557-61. Web.

Doenicke, Alfred W., Michael F. Roizen, and Jens Rau. "Reducing Pain During Propofol Injection." Anesthesia Analgesia 62.3 (1996): 472-74. Web.

Jalota, L., V. Kalira, and E. George. "Prevention of Pain on Injection of Propofol: Systematic Review and Meta-analysis." British Medical Journal 342.Mar. 15 1 (2011): D1110. Web.

Lee, J.-R., C.-W. Jung, and Y.-H. Lee. "Reduction of Pain during Induction with Target-controlled Propofol and Remifentanil." British Journal of Anaesthesia 99.6 (2007): 676-80. Web.

Li Aimin, Quanxing Zhang, and Gencheng Zhang. "Adsorption of Phenolic Compounds from Aqueous Solutions by a Water-compatible Hypercrosslinked Polymeric Adsorbent." Chemosphere 47.9 (2002): 981-89. Web.

Sundarathiti, Petchara, Nuanjai Boonthom, and Theerawat Chalacheewa. "Comparison of Propofol-LCT with Propofol-LCT/MCT on Pain of Injection." J Med Assoc Thai 90.12 (2007): n. pag. Web.

* cited by examiner

METHOD AND APPARATUS FOR PURIFYING THE DISPERSING LIQUID IN A COLLOIDAL DISPERSION

TECHNICAL FIELD

The present application is directed to a purification system for a colloidal dispersion containing an unwanted dissolved substance (or substances) in the dispersing liquid phase and more particularly to a filter device that can be used at the time of operation.

BACKGROUND

Propofol is a widely used anesthetic agent in the United States due to its rapid onset and short duration of action. Propofol is a non-polar molecule, which currently is administered using an emulsion formulation. Diprivan® is a common formulation of propofol and is a lipid microemulsion whereby propofol is dissolved in a small variety of oils, most commonly soybean oil, and is then emulsified with lecithin as a stabilizing agent. One major drawback of this microemulsion is the occurrence of pain on injection of the propofol emulsion (Sundarathiti et al., 2007). It has been reported that pain is observed approximately 60% of the time (Jalota et al. 2011). A cause of the pain on injection has been attributed to the concentration of free propofol in the aqueous phase of the emulsion (Doenicke et al. 1996). Various interventions have been tried to reduce the pain on injection, which include using lidocaine, opioids, or remifentanil prior to injection (Lee et al. 2007), and the use of the antecubital vein or hand vein with occlusion (Jalota et al. 2011). These techniques have failed to gain widespread popularity and the search for alternative interventions continues.

Another safety issue associated with the use of propofol formulations is hemolysis. According to Weihui et al. (2012), propofol formulations with low in vitro hemolytic activity were likely to have a low free propofol concentration in the aqueous phase. The reason for this may be due to the high affinity of propofol within the red blood cell membrane due to its high lipid content. As a result, much work has been done to develop new emulsion formulations, including microemulsions that naturally have lower concentrations of free propofol in the aqueous phase.

These drawbacks are evidence of free propofol in the emulsion. The propofol concentration in the aqueous phase of the current drug, Diprivan, has been reported as 18.571 µg/ml (Babl et al., 1995). An approach to reduce the concentration of free propofol could be the development of a small adsorptive filtering device that removes and/or reduces the level of free propofol at the time the emulsion is injected into the patient. For example, the filtering device might contain an adsorbent material such as activated carbon (charcoal), a water compatible hypercrosslinked polymeric adsorbent that provides binding sites of the propofol in the aqueous phase (Li et al., 2002), or even lipid-based materials that have a high partition coefficient of propofol. In a study by Davies et al. (2002), microfiltration of a propofol emulsion was explored as a way to decrease propofol induced pain on injection. An effect was observed, but it wasn't clear what the mechanism of action was. Since the filter membrane must allow the oil droplet phase of the emulsion (which contains the bulk of the drug propofol) to pass through, this limits the kinds of filters membranes that can be used since they could be easily clogged by the oil droplet phase.

There is therefore a need to provide a purification system that works with liquid colloidal dispersions including emulsion formulations, such as those containing propofol, with the goal to remove a dissolved substance (or substances) from the dispersing liquid phase (such as free-propofol) at the time of use.

SUMMARY

To overcome the above difficulties, a filter device is disclosed whereby a portion of the dispersing liquid phase is forced across a filter membrane whereby the unwanted dissolved substance can be removed by adsorption and subsequently is recombined with the unfiltered colloidal dispersion to produce a purified colloidal dispersion. In one embodiment, a two stage hollow fiber filter device is described whereby the second filter stage has a smaller number of hollow fibers compared to the first stage. This is to create a back-pressure on the colloidal dispersion in the first stage which forces a portion of the dispersing liquid across the filter membrane in the first stage. The filter membrane used in this embodiment is made from an adsorptive material that binds the unwanted dissolved substance. In a second embodiment, the same number of fibers are used in the second filter stage, however, an orifice is included between the two filter stages to create the back-pressure and flow of a portion of dispersing liquid across the first filter stage membrane. In a third embodiment, the same number of fibers are used in the respective stages, however, a significant portion of the fibers in the second stage are blocked at the inlet end to prevent flow of the colloidal dispersion into these hollow fibers. This effectively creates the back-pressure while allowing more surface area for adsorption of the unwanted dissolved substance to occur. In a fourth embodiment, a sheet membrane is described for both filter stages, further including an orifice between the two stages to create the back-pressure, however, an adsorptive media is filled in the internal space of the filter where adsorption can occur. A fifth embodiment of a filter device is described whereby the first stage is configured in a U-shape as a means to simplify the manufacturing of the filter device. A sixth embodiment incorporates a fluid pump and a Venturi device as a means to create the flow of a portion of the dispersing liquid phase across a first filter stage. The Venturi device serves to create both a back-pressure on the filter stage as well as create a reduced pressure that draws the purified dispersing liquid back into the bulk flow of the colloidal dispersion where they are mixed together.

DETAILED DESCRIPTION OF PREFERRED EMBODIMENTS

Figure 1:
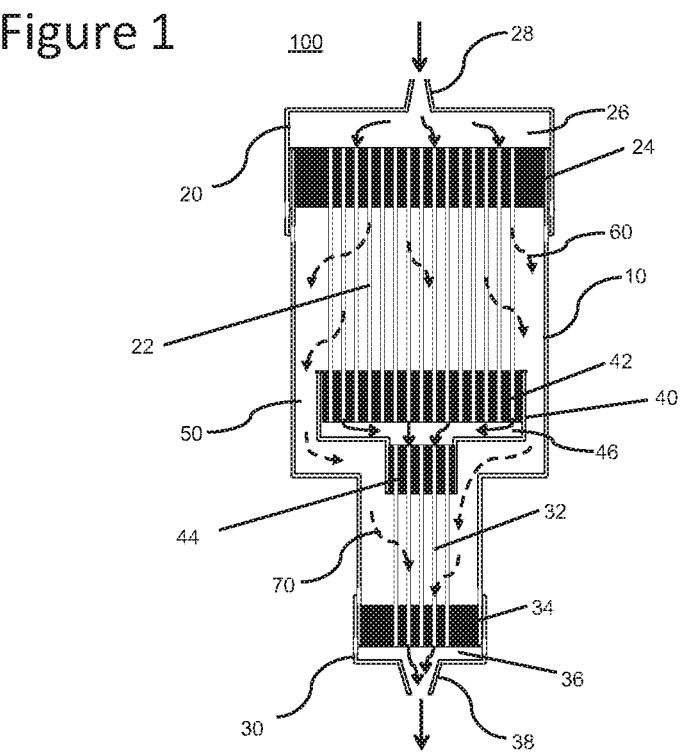
FIG. 1 is a side perspective view of a purification system for a colloidal dispersion in accordance with one embodiment.

According to a first embodiment, a filtering device 100 is shown in FIG. 1 which consists of a filter casing 10 having an inlet header cap 20 attached at one end of the filter casing and an outlet header cap 30 attached at the other end of the casing. A filter inlet port 28 is associated with the inlet header cap 20 for receiving a colloidal suspension (dispersion) to be purified and a filter outlet port 38 is associated with the outlet header cap 30 for delivering the purified colloidal suspension. The unpurified colloidal suspension is such that it contains an unwanted dissolved substance in the continuous phase (or dispersing liquid) which is to be removed or reduced upon passing through the filtering device. An example of this is an oil-water emulsion containing the drug propofol, whereby the aqueous (water) phase contains a high level of propofol (free-propofol) which is believed to be associated with an increased pain upon injection.

The filter casing 10 includes a first filtering stage consisting of a set of hollow fiber filtering elements 22 that are potted with a potting compound 24 at the inlet side of the casing, thus forming an inlet header space 26 in association with the inlet header cap 20. The filter casing includes a second filtering stage consisting of a second set of hollow fiber filtering elements 32 that are potted with a potting compound 34 at the outlet side of the casing, thus forming an outlet header space 36 in association with the outlet header cap 30. Further, an inter-stage header connector 40 is used to join the two hollow fiber filtering stages internally whereby a potting compound 42 seals the distal ends of the first set of hollow fibers 22 to the inter-stage header 40 and a potting compound 44 seals the proximal ends of the second set of hollow fibers 32 to the inter-stage header connector 40 and thereby forming an inter-stage header space 46 that serves as a conduit between the lumen side of the two hollow fiber stages 22 and 32, respectively. The inter-stage header connector also serves to create an extra-luminal space 50 that is formed between the inside of the filter casing 10, the outside of the inter-stage header connector 40, and the outside of the two hollow fiber filtering stages 22 and 32. The pore size of the filtering elements used are such that it allows the aqueous phase (or dispersion liquid) of the emulsion to pass through the filter elements, but prevents the oil droplets (or colloidal particles) of dispersed phase to pass through. In this embodiment, the number of hollow fibers in the second filtering stage 32 is considerably less than number of hollow fibers contained in the first filtering stage 22, and the filter (membrane) is constructed from an adsorptive media which serves to remove the unwanted dissolved substance from the aqueous phase.

Operation of the filtering device 100 is described as follows. First, the unpurified colloidal suspension (or emulsion) enters the inlet port 28 and flows into inlet header space 26 and is distributed into the lumen side of the first set of hollow fibers 22 making up the first filtering stage of the device. The emulsion then travels down through the lumen side of the first filter stage and enters into the inter-stage header space 46 where it is directed into the lumen side of the second filter stage 32. Because the number of hollow fibers in the second stage is considerably less than the first stage, a backpressure develops relative to the emulsion contained in first stage which leads to a filtration of a portion of the aqueous phase 60 through the hollow fiber membrane walls of the first filter stage 22. The passing of this aqueous phase through the membrane wall serves to reduce the concentration of the unwanted dissolved substance due to adsorption to the membrane surface. For the example described here, use of a hydrophobic membrane material such as polysulphone will serve as an adsorptive media whereby free propofol in the aqueous phase adsorbs to the membrane surface as a result of hydrophobic bonding. As the extra-luminal space 50 fills with the aqueous phase of the emulsion, the pressure inside this space will build up and begin to flow in a reverse direction across the membrane walls 70 of the second set of hollow fibers 32. This results because the pressure of the emulsion flowing through the lumen side of the hollow fibers of the second stage 32 is lower relative to the extra-luminal space 50 due to it being nearer to the filter outlet 38 and due to the more concentrated emulsion on the lumen side in this stage which serves to draw in the aqueous phase from the extra-luminal space caused by osmotic pressure. As the aqueous phase passes through the membrane wall of the second filter stage 32, further adsorption of the unwanted dissolved substance will occur. The twice filtered aqueous phase then recombines with the concentrated emulsion phase passing through the lumen side of the second set of hollow fibers 32 to create a purified emulsion which enters the outlet header space 36 and exits the filter through the outlet port 38.

Figure 2:
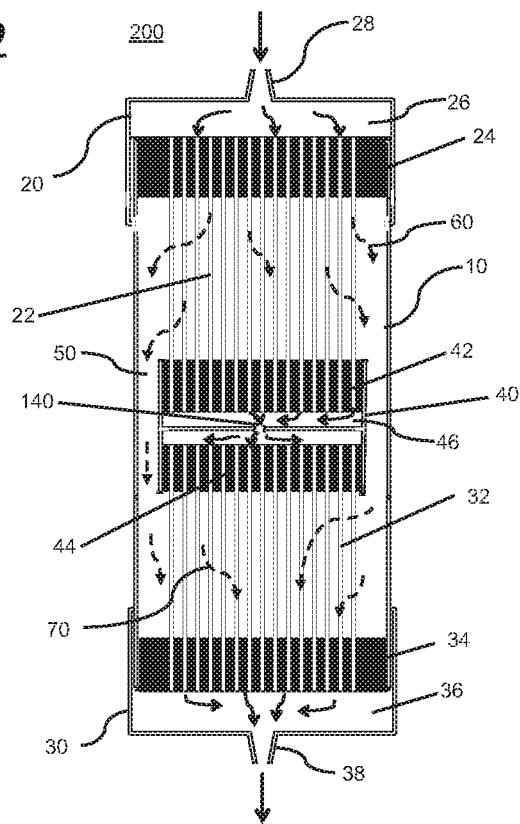
FIG. 2 is a side perspective view of a purification system for a colloidal dispersion in accordance with one embodiment.

According to a second embodiment of the invention as shown in FIG. 2, a similar number of hollow fibers are used in each of the two filtering stages 22 and 32, respectively, however, an orifice feature 140 is integrated as part of the inter-stage header connector 40. In this embodiment, the orifice serves to create the necessary backpressure in the first filter stage 22 to cause the filtration of a portion of the aqueous phase 60 across the membrane wall. The advantage of this is that the additional number of hollow fibers used in the second stage 32 allows for additional membrane surface area for which adsorption of the unwanted dissolved substance can occur. This can result in better performance of the filter device by achieving either a lower concentration of the unwanted dissolved substance in the aqueous phase or being capable to purify a larger volume of the emulsion or colloidal suspension.

Figure 3:
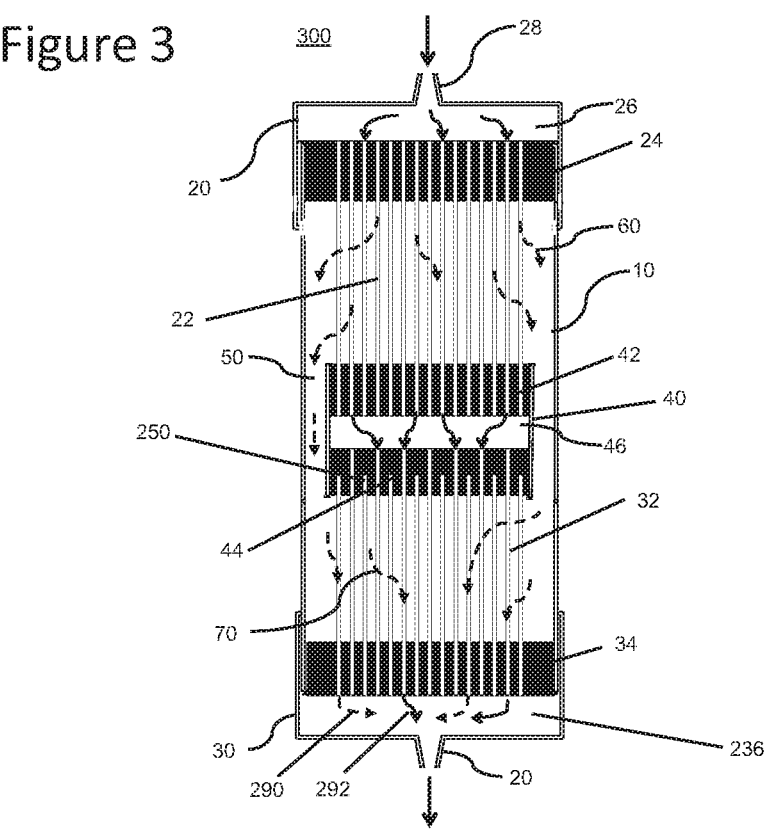
FIG. 3 is a side perspective view of a purification system for a colloidal dispersion in accordance with one embodiment.

According to a third embodiment as shown in FIG. 3, a similar number of hollow fibers are used in each of the two filtering stages 22 and 32, respectively, however, the potting of the second set of hollow fibers in the inter-stage header cap 40 is such that a considerable portion of hollow fibers are blocked at the inlet side 250 in the potting compound 44. Similar to the first embodiment, the fewer number of open hollow fibers in the second set of hollow fibers will cause a backpressure of the emulsion in the first stage which leads to the filtration of the aqueous phase 60 from the first stage of hollow fibers. In this embodiment, however, some of the once filtered aqueous phase will be reversed filtered into the lumens of the set of blocked hollow fibers 250, noting that that these hollow fibers do not contain the concentrated emulsion because of the blockage at the potting compound 40. As such, the outlet header space 236 serves as a mixing chamber to fully combine the fluids exiting from both the blocked hollow fibers 290 and unblocked hollow fibers 292 of the second filter stage 32. The advantage of this is that it allows for additional membrane surface area for which adsorption of the unwanted dissolved substance can occur similar to the second embodiment, but does not require the additional orifice feature of this embodiment.

Figure 4:
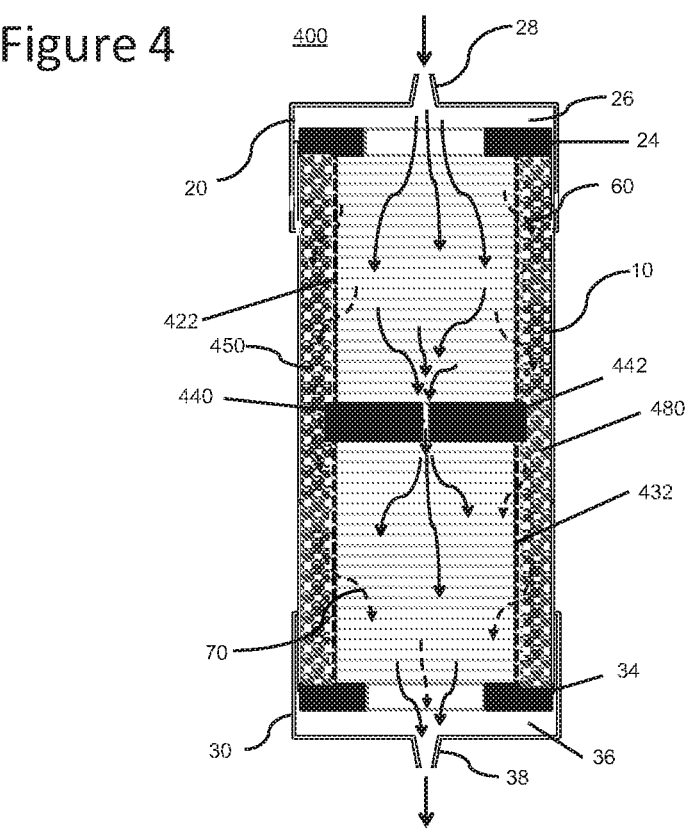
FIG. 4 is a side perspective view of a purification system for a colloidal dispersion in accordance with one embodiment.

In FIG. 4, a fourth embodiment is shown whereby flat sheet membranes 422 and 432 are used instead of hollow fiber membranes 22 and 32, respectively for the first and second filter stages. The flat sheet may be a formed into a pleated sheet membrane as known in the art and is potted at each end in order to provide a seal that prevents the unpurified emulsion from entering the trans-membrane casing space 450. This embodiment also includes a potting compound 442 connecting the two filter stages which includes the orifice feature 440 encased and/or formed as an integral part of this potting compound. Another feature of this embodiment is the addition of an adsorptive media 480 that is limited to the trans-membrane casing space 450 of the device. This serves to provide additional surface area for removal of the unwanted chemical contained in the aqueous phase of the emulsion.

Figure 5:
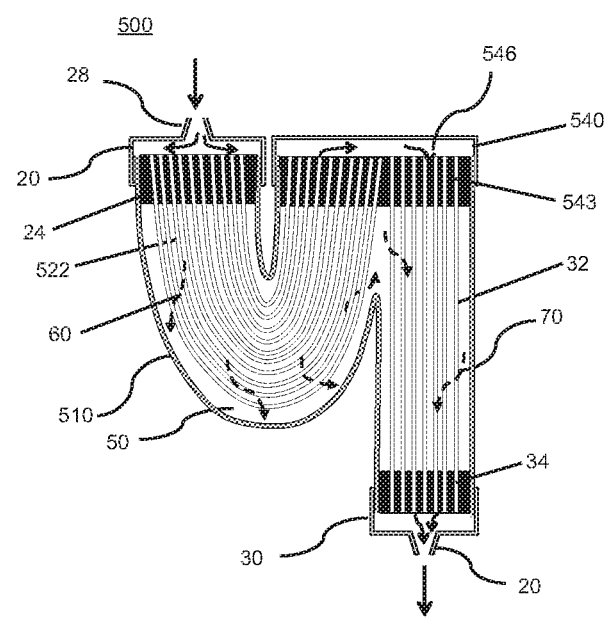
FIG. 5 is a side perspective view of a purification system for a colloidal dispersion in accordance with one embodiment.

In a fifth embodiment shown in FIG. 5, construction of the filter device is altered whereby the filter casing 510 is such that the first filter stage 522 can be arranged in a U-shaped configuration such that distal ends of the hollow fibers from the first stage 522 and the proximal ends of the hollow fibers from the second stage are potted into a single potting compound 543 that lies in a similar proximity to the potting compound 24 which seals the proximal ends of the first filter stage hollow fibers to the filter casing at the inlet end of the filter device. Further, the potting compound 543 seals the outside of hollow fibers to a third opening of the filter casing whereby an inter-stage header cap 540 is attached to create the inter-stage header space 546. In this manner, a conduit is formed such that the lumen side of the first hollow fiber stage 522 and the lumen side of the second hollow fiber stage 32 such that operation is similar to that described in the first embodiment. This may have certain advantages with respect to manufacturing of the filter device as it reduces the number of distinct potting compound regions and thereby reduces the number of steps required to produce the filter device.

Figure 6:
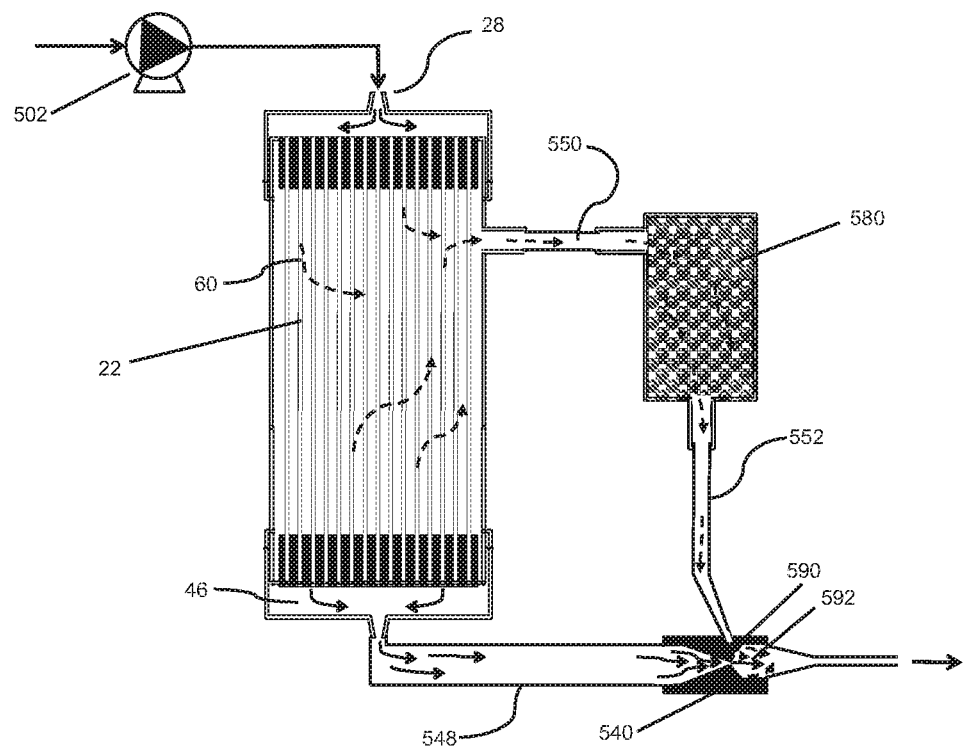
FIG. 6 is a side perspective view of a purification system for a colloidal dispersion in accordance with one embodiment.

A method of purifying a colloidal suspension that contains an unwanted dissolved substance in the aqueous phase is shown in FIG. 6. In this embodiment, a fluid pump 502 as known in the art is used to deliver the unpurified colloidal suspension to the inlet port 28 of a filter device. Similar to the previous embodiments, the filter device contains an adsorptive type filter membrane 22 that separates the filter device into an upstream compartment and a downstream compartment. The upstream compartment is fluidly connected to a header space 46 that in turn is fluidly connected to a first conduit 548. The downstream compartment is fluidly connected to a second conduit 550 and a third conduit 552, further containing an adsorptive device 580 for additional purification of the aqueous phase of the suspension. Conduits 548 and 552 are connected to the inlet and vacuum ports, respectively of a Venturi-type device 540 as is known in the art. Operation is such that the inlet pump 502 forces flow of the suspension through the nozzle of the Venturi device causing an increase of velocity and a decrease in pressure (or vacuum) at the outlet of the nozzle. The effect is such that there is an increase in pressure before the nozzle of the Venturi device causing a flow of the aqueous phase 60 across the filter membrane 22 and a lower (and possibly negative) pressure at the exit of the nozzle which will further draw the filtered aqueous phase into conduit 550 and through the adsorptive device 580. The Venturi device 140 further serves as a mixing chamber whereby the purified aqueous phase 590 is combined back with the concentrated emulsion phase to produce the purified emulsion.

It should be understood to those skilled in the art that the above embodiments show the technical elements of the device and that varying combinations of these elements can be used to achieve the same or similar results.

What is claimed:

1. A filter device for use in a purification system for a colloidal dispersion consisting of a particle phase and a liquid dispersing phase, said liquid dispersing phase containing at least one unwanted dissolved substance to be removed by the filter device, said device comprising:

a housing comprised of a casing, an inlet header cap, and an outlet header cap, said inlet header cap including an inlet port for receiving an unpurified colloidal dispersion and said outlet header cap including an outlet port for discharging a purified colloidal dispersion;

a first set of hollow fiber semi-permeable filter elements within said housing, said first hollow fiber filter elements being permeable to the liquid dispersing phase of the colloidal dispersion while not being permeable to the particle phase, said first set of hollow fiber filter elements having a first end and a second end, said first end being potted with a first potting compound forming an inlet header space within said housing, said inlet header space being in fluid communication with said inlet port and a lumen side of the first set of hollow fiber filter elements;

a second set of hollow fiber semi-permeable filter elements within said housing, said second set of filter elements being permeable to the liquid dispersing phase of the colloidal dispersion while not being permeable to the particle phase, said second set of hollow filter elements having a first end and a second end, said second end being potted with a second potting compound forming an outlet header space within said housing, said outlet header space being in fluid communication with said outlet port and a lumen side of the second set of hollow fiber filter elements;

an inter-stage header connector within said housing, said inter-stage header connector including a third potting compound used to pot said second end of the first set of hollow fiber filter elements and a fourth potting compound used to pot said first end of second set of hollow fiber filter elements, both the third and fourth potting compounds forming an inter-stage header space which is in fluid communication with the lumen side of hollow fibers making up both the first set and second set of hollow fiber filter elements, and an extra-luminal space formed between the inside of the casing, an outside of the inter-stage header connector, and an outside of the first and second sets of hollow fiber filter elements;

an adsorptive material capable of binding the at least one unwanted dissolved substance from the liquid dispersing phase, said adsorptive material being a material used to construct the second set of hollow fiber filter elements; and whereby said second set of hollow fiber filter elements are configured with a reduced number of hollow fiber filter elements relative to the number of hollow fiber filter elements making up the first set of hollow fiber filter elements and which function as a flow restrictive feature when flow of the colloidal dispersion is introduced into the inlet port of the device, further resulting in an elevated fluid pressure inside the lumens of the first set of hollow fiber filter elements relative to that inside the lumens of the second set of hollow fiber filter elements and causing a portion of the liquid dispersing phase of the colloidal dispersion to pass through the first set of hollow fiber filter elements and into the extra-luminal space, then further passing through the second set of hollow fiber filter elements where it recombines with the colloidal dispersion flowing through the hollow fiber lumens of the second set of hollow fiber filter elements and whereby adsorption of the at least one unwanted substance occurs when the portion of the liquid dispersing phase passes through and is in contact with surfaces of the first and second set of hollow fiber filter elements prior to recombining with the colloidal dispersion and exiting through the outlet port as a purified colloidal dispersion.

2. The filter device of claim 1, whereby the material used to construct the second set of hollow fiber filter elements includes a hydrophobic material.

3. The filter device of claim 1, whereby the material used to construct the second set of hollow fiber filter elements includes the material polysulfone.

4. The filter device of claim 1, whereby a portion of the lumen side of the hollow fiber filter elements are blocked at the first end of the second set of hollow fiber filter elements by the fourth potting compound at a luminal entrance of the second set of hollow fiber filter elements.

5. A filter device for use in a purification system for a colloidal dispersion consisting of a particle phase and a liquid dispersing phase, said liquid dispersing phase containing at least one unwanted dissolved substance to be removed by the filter device, said device comprising:
　a housing comprised of a casing, an inlet header cap, and an outlet header cap, said inlet header cap including an inlet port for receiving an unpurified colloidal dispersion and said outlet header cap including an outlet port for discharging a purified colloidal dispersion;
　a first set of hollow fiber semi-permeable filter elements within said housing, said first set of hollow fiber filter elements being permeable to the liquid dispersing phase of the colloidal dispersion while not being permeable to the particle phase, said first set of hollow fiber filter elements having a first end and a second end, said first end being potted with a first potting compound forming an inlet header space within said housing, said inlet header space being in fluid communication with said inlet port and a lumen side of the first set of hollow fiber filter elements;
　a second set of hollow fiber semi-permeable filter elements within said housing, said second set of hollow fiber filter elements being permeable to the liquid dispersing phase of the colloidal dispersion while not being permeable to the particle phase, said second set of hollow fiber filter elements having a first end and a second end, said second end being potted with a second potting compound forming an outlet header space within said housing, said outlet header space being in fluid communication with said outlet port and a lumen side of the second set of hollow fiber filter elements;
　an inter-stage header connector within said housing, said inter-stage header connector including a third potting compound used to pot said second end of the first set of hollow fiber filter elements and a fourth potting compound used to pot said first end of second set of hollow fiber filter elements, both the third and fourth potting compounds forming an inter-stage header space which is in fluid communication with the lumen side of hollow fibers making up both the first set and second set of hollow fiber filter elements, and an extra-luminal space formed between the inside of the casing, an outside of the inter-stage header connector, and an outside of the first and second sets of hollow fiber filter elements;
　an adsorptive material capable of binding the at least one unwanted dissolved substance from the liquid dispersing phase, said adsorptive material being a material used to construct the second set of hollow fiber filter elements; and
　an orifice positioned within the inter-stage header space that functions as a flow restrictive feature when flow of the colloidal dispersion is introduced into the inlet port of the device, further resulting in an elevated fluid pressure inside the lumens of the first set of hollow fiber filter elements relative to that inside the lumens of the second set of hollow fiber filter elements and causing a portion of the liquid dispersing phase of the colloidal dispersion to pass through the first set of hollow fiber filter elements and into the extra-luminal space, then further passing through the second set of hollow fiber filter elements where it recombines with the colloidal dispersion flowing through the hollow fiber lumens of the second set of hollow fiber filter elements and whereby adsorption of the at least one unwanted substance occurs when the portion of the liquid dispersing phase passes through, and is in contact with the surfaces of the first and second set of hollow fiber filter elements prior to recombining with the colloidal dispersion and exiting through the outlet port as a purified colloidal dispersion.

6. A filter device for use in a purification system for a colloidal dispersion consisting of a particle phase and a liquid dispersing phase, said liquid dispersing phase containing at least one unwanted dissolved substance to be removed by the filter device, said device comprising:
　a housing comprised of a casing, an inter-stage header cap, an inlet header cap, and an outlet header cap, said inlet header cap including an inlet port for receiving an unpurified colloidal dispersion and said outlet header cap including an outlet port for discharging a purified colloidal dispersion;
　a first set of hollow fiber semi-permeable filter elements within said housing, said first hollow fiber filter elements being permeable to the liquid dispersing phase of the colloidal dispersion while not being permeable to the particle phase, said first hollow fiber filter elements having a first end and a second end, said first end being potted with a first potting compound forming an inlet header space within said housing, said inlet header space being in fluid communication with said inlet port and a lumen side of the first set of hollow fiber filter elements;
　a second set of hollow fiber semi-permeable filter elements within said housing, said second set of hollow fiber filter elements being permeable to the liquid dispersing phase of the colloidal dispersion while not being permeable to the particle phase, said second set of hollow fiber filter elements having a first end and a second end, said second end being potted with a second potting compound forming an outlet header space within said housing, said outlet header space being in fluid communication with said outlet port and a lumen side of the second set of hollow fiber filter elements;
　a third potting compound used to pot said second end of the first set of hollow fiber filter elements and said first end of second set of hollow fiber filter elements, said third potting compound and inter-stage header cap forming an inter-stage header space which is in fluid communication with the lumen side of hollow fibers making up both the first set and second set of hollow fiber filter elements, and an extra-luminal space formed between the inside of the casing and an outside of the first and second sets of hollow fiber filter elements;

an adsorptive material capable of binding the at least one unwanted dissolved substance from the liquid dispersing phase, said adsorptive material being a material used to construct the second set of hollow fiber semi-permeable filter elements; and whereby said second set of hollow fiber filter elements are configured with a reduced number of hollow fiber filter elements relative to the number of hollow fiber elements making up the first set of hollow fiber elements and which function as a flow restrictive feature when flow of the colloidal dispersion is introduced into the inlet port of the device, further resulting in an elevated fluid pressure inside the lumens of the first set of hollow fiber filter elements relative to that inside the lumens of the second set of hollow fiber filter elements and causing a portion of the liquid dispersing phase of the colloidal dispersion to pass through the first set of hollow fiber filter elements and into the extra-luminal space, then further passing through the second set of hollow fiber filter elements where it recombines with the colloidal dispersion flowing through the hollow fiber lumens of the second set of hollow fiber filter elements and whereby adsorption of the at least one unwanted substance occurs when the portion of the liquid dispersing phase passes through, and is in contact with surfaces of the first and second set of hollow fiber filter elements prior to recombining with the colloidal dispersion and exiting through the outlet port as a purified colloidal dispersion.

* * * * *